(12) United States Patent
Tanaka (10) Patent No.: US 9,095,165 B2
(45) Date of Patent: Aug. 4, 2015

(54) PROPHYLACTIC/AMELIORATING AGENT FOR ADULT DISEASES COMPRISING 5-AMINOLEVULINIC ACID, DERIVATIVE OF 5-AMINOLEVULINIC ACID, OR SALT OF 5-AMINOLEVULINIC ACID OR THE DERIVATIVE OF 5-AMINOLEVULINIC ACID AS ACTIVE INGREDIENT

(75) Inventor: Tohru Tanaka, Saitama (JP)

(73) Assignee: SBI Pharmaceuticals Co., Ltd., Tokyo (JP)

( * ) Notice: Subject to any disclaimer, the term of this patent is extended or adjusted under 35 U.S.C. 154(b) by 291 days.

(21) Appl. No.: 13/123,374

(22) PCT Filed: Oct. 27, 2009

(86) PCT No.: PCT/JP2009/005651
§ 371 (c)(1),
(2), (4) Date: Apr. 8, 2011

(87) PCT Pub. No.: WO2010/050179
PCT Pub. Date: May 6, 2010

(65) Prior Publication Data
US 2011/0196033 A1  Aug. 11, 2011

(30) Foreign Application Priority Data

Oct. 27, 2008 (JP) ................................ 2008-275914

(51) Int. Cl.
| | |
|---|---|
| A61K 31/198 | (2006.01) |
| A61K 31/295 | (2006.01) |
| A61K 33/26 | (2006.01) |
| A23L 1/305 | (2006.01) |
| A23L 1/30 | (2006.01) |
| A23L 1/304 | (2006.01) |
| A61K 31/197 | (2006.01) |
| A61K 31/555 | (2006.01) |
| A61K 45/06 | (2006.01) |

(52) U.S. Cl.
CPC ............... *A23L 1/3051* (2013.01); *A23L 1/30* (2013.01); *A23L 1/304* (2013.01); *A23L 1/3045* (2013.01); *A61K 31/197* (2013.01); *A61K 31/198* (2013.01); *A61K 31/295* (2013.01); *A61K 31/555* (2013.01); *A61K 33/26* (2013.01); *A61K 45/06* (2013.01)

(58) Field of Classification Search
None
See application file for complete search history.

(56) References Cited

U.S. PATENT DOCUMENTS

| 5,753,706 A | 5/1998 | Hsu | |
| 2003/0054014 A1 | 3/2003 | Chung et al. | |
| 2003/0158258 A1 | 8/2003 | Marti et al. | |
| 2003/0170315 A1 | 9/2003 | Makino | |
| 2004/0048842 A1 | 3/2004 | McMillan | |
| 2004/0234555 A1 | 11/2004 | Oshida et al. | |
| 2007/0249721 A1 | 10/2007 | Ito | |
| 2007/0281906 A1* | 12/2007 | Dalton et al. | 514/80 |
| 2008/0026075 A1* | 1/2008 | Kondo et al. | 424/630 |
| 2009/0047304 A1 | 2/2009 | Takahashi et al. | |
| 2009/0130227 A1 | 5/2009 | Ito | |

FOREIGN PATENT DOCUMENTS

| EP | 2135613 A1 * | 12/2009 |
| JP | 05-252898 A | 10/1993 |
| JP | 06-065031 A | 3/1994 |
| JP | 08-081381 A | 3/1996 |
| JP | 2731032 B2 | 12/1997 |
| JP | 10-295325 A | 11/1998 |
| JP | 2001-506262 A | 5/2001 |
| JP | 2002-027929 A | 1/2002 |
| JP | 2002-080376 A | 3/2002 |
| JP | 2002-512205 A | 4/2002 |
| JP | 2002-138027 A | 5/2002 |
| JP | 2003-040770 A | 2/2003 |
| JP | 2004-131482 A | 4/2004 |
| JP | 2006-124372 A | 5/2006 |
| JP | 3810018 B2 | 8/2006 |
| JP | 2007-238441 A | 9/2007 |

(Continued)

OTHER PUBLICATIONS

Rolo et al., Diabetes and mitochondrial function: role of hyperglycemia and oxidative stress, Toxicology and Applied Pharmacology 212 (2006) 167-178.*

(Continued)

*Primary Examiner* — Svetlana M Ivanova (74) *Attorney, Agent, or Firm* — Foley & Lardner LLP (57) ABSTRACT

It is to provide a pharmaceutical composition which is different from an existing therapeutic agent of an adult disease, of a biochemical reaction-inhibiting type, and which action mechanism is to improve the basal metabolism, wherein the composition has no side effects, and does not generate drug resistance against adult disease; and a method for preventing/treating an adult disease by using the same. It is to provide a composition for preventing/ameliorating an adult disease such as metabolic syndrome, diabetes, hyperlipidemia, hypertension, impaired liver function, renal failure, adiposity, erectile dysfunction, menopausal disorder, shoulder discomfort, and low back pain, comprising 5-aminolevulinic acid (ALA), its derivative, or salt thereof, preferably comprising ALA, its derivative, or salt thereof, and an iron compound such as sodium ferrous citrate, iron sodium citrate and iron ammonium citrate; a food or food material for preventing/ameliorating an adult disease comprising the composition; and a method for using the composition for preparing an agent for preventing/ameliorating an adult disease.

3 Claims, 5 Drawing Sheets

(56) References Cited

FOREIGN PATENT DOCUMENTS

| | | |
|---|---|---|
| JP | 3991063 B2 | 10/2007 |
| JP | 2008-255059 A | 10/2008 |
| WO | WO 91/01727 A2 | 2/1991 |
| WO | WO 98/26776 A1 | 6/1998 |
| WO | WO 99/53962 A1 | 10/1999 |
| WO | WO 2006/025286 A1 | 3/2006 |
| WO | WO 2007/089571 A2 | 8/2007 |
| WO | WO 2009/139156 A1 | 11/2009 |

OTHER PUBLICATIONS

Itakura et al., "Metabolic Syndrome and Oxidative Stress," Clinical Nutrition, 2006, 108(6):777-783, Special Issue, with English translation, 8 pages.

Hyodo, Akira, "Menopausal Syndrome," Clinical Journal of Traditional Chinese Medicine, 1993, 14(4):78(422)-81(425), with English translation, 9 pages.

Inoue et al., "Clinical experience with intravesical instillations of 5-aminolevulinic acid (5-ALA) for the photodynamic diagnosis using fluorescence cystoscopy for bladder cancer," Journal of Japanese Urological Association, 2006, 97(5)Supp:719-729, with English translation, 16 pages.

Nakao et al., "Oxidative stress in the progression of renal damage, in the end stage of renal disease and in the dialysis therapy," Sanka Stress Free Radical Igaku Seibutsugaku no Siazensen, ver. 2, Ishiyaku Pub., Inc., 2006, 322-325, with English translation, 9 pages.

Zhao et al., "Effect of dietary iron on metabolism in diet-induced obese rats," Zhongguo Gonggong Weisheng, 2006, 22(1):74-76, one page English abstract.

Pandey et al., "Enhanced Production of High-Quality Biomass, σ-Aminolevulinic Acid, Bilipigments, and Antioxidance Capacity of a Food Alga *Nostochopsis lobatus*," Appl. Biochem. Biotechnol., 2008, 140:221-231.

International Search Report mailed Feb. 2, 2010, in PCT/JP2009/005651, 6 pages.

Itakura et al., "Metabolic Syndrome to Sanka Stress," Rinsho Eiyo, 2006, 108(6):777-783.

Hyodo, Akira, "Konenki Shogai," Journal of Traditional Chinese Meciicine, 1993, 14(4):422-425.

Inoue et al., "Clinical experience with intravesical instillations of 5-aminolevulinic acid (5-ALA) for the photodynamic diagnosis using fluorescence cystoscopy for bladder cancer," Journal of Japanese Urological Association, 2006, 97(5):719-729.

Jeremy et al., "Reactive oxygen species and erectile dysfunction: possible role of NADPH oxidase," International Journal of Impotence Research, 2007, 19:265-280.

Kennedy et al., "Photodynamic Therapy with Endogeneous Protoporphyrin IX: Basic: Principles and Present Clinical Experience," Journal of Photochemistry and Photobiology, B: Biology, 1990, 6:143-148.

McGillion et al., "Some pharmacological effects of σ-aminoloaevulinic acid on blood pressure in the rat and on rabbit isolated ear arteries," Clinical and Experimental Pharmacology and Physiology, 1975, 2:365-371.

Nakao et al., "Oxidative stress in the progression of renel damage, in the end stage of renal disease and in the dialysis therapy," Sanka Stress Free Radical Igaku Seibutsugaku no Siazensen, ver. 2, Ishiyaku Pub., Inc., 2006, 322-325.

Zhao et al., "Effects of dietary iron on metabolism in diet-induced obese rats," Zhongguo Gonggong Weisheng, 2006, 22(1):74-76.

\* cited by examiner

53 years old men by ALAIron (5-ALA H$_3$PO$_4$ 25mg + Iron /day)
insulin 10 5 10

Fig. 6

70 years old men by ALAIron (5-ALA H$_3$PO$_4$ 10mg + Iron /day)

Fig. 7

72 years old women by ALAIron (5-ALA H$_3$PO$_4$ 50mg + Iron /day)

Fig. 8

69 years old women by ALAIron (5-ALA H$_3$PO$_4$ 15mg + Iron /day)

Fig. 9

Analysis of safety test on healthy person (25mg/day)

Fig. 10

PROPHYLACTIC/AMELIORATING AGENT FOR ADULT DISEASES COMPRISING 5-AMINOLEVULINIC ACID, DERIVATIVE OF 5-AMINOLEVULINIC ACID, OR SALT OF 5-AMINOLEVULINIC ACID OR THE DERIVATIVE OF 5-AMINOLEVULINIC ACID AS ACTIVE INGREDIENT

TECHNICAL FIELD

The present invention relates to an agent for ameliorating/preventing an adult disease comprising 5-aminolevulinic acid (herein after also referred to as "ALA"), its derivative, or salts thereof as an active ingredient. Specifically, the present invention relates to a composition for preventing/ameliorating an adult disease such as diabetes, hyperlipidemia, or hypertension, which is administered orally, by intravenous injection, sublingual tablet, intraperitoneal administration, entral fluid, transdermal agent, or suppository, or to a method for preventing/ameliorating the same.

BACKGROUND ART

Adult disease is a generic expression for disease and pathology including diabetes, hyperlipidemia, hypertension, impaired liver function, renal failure, adiposity, erectile dysfunction, menopausal disorder, shoulder discomfort, and low back pain. Formerly, it was thought that these diseases developed with aging. However, recently, it has been revealed that lifestyle habits for a long time are strongly associated with the onset as a so-called lifestyle-related disease. It is believed that the onset and development mechanism of each disease are associated with each other, and the state wherein hypertension, hyperlipidemia, or diabetes is combined with adiposity is called specifically metabolic syndrome, to which caution is raised. However, there is no particular therapeutic agent, treatment method, preventative agent or preventing method for it. The present situation is that the medical staffs or patients are unnecessarily confused.

Adult diseases decrease significantly the quality of patient's life, and there is a risk of complications. Particularly, the number of patients is rapidly increasing in developed countries. While number of medicines for preventing/ameliorating an adult disease has been developed, each of them is an agent for ameliorating individual symptom, such as lowering blood glucose level of diabetes, lowering blood pressure, or lowering cholesterol levels, and the action mechanism is mostly the inhibition of a particular enzyme, etc.

For example, concerning diabetes, currently most of the diabetes is a so-called type II diabetes, being insulin resistant, and agents for inhibiting glucose metabolism or agents for suppressing absorption from foods have been developed. It is said that these inhibitors or agents for suppressing absorption are exerting a certain effect. However, as the radical cause of diabetes onset is a diminished ability to absorb sugar into cells, it is thought that an approach of suppressing furnishing sugar to cells or blood is not an essential solution, leading to decrease of life activation of the patient.

Concerning hyperlipidemia, health foods targeting suppression of fat absorption or agents inhibiting cholesterol metabolism (i.e. statin agents) are fulfilling market needs. However, it is known that while statin agents etc. decrease significantly cholesterol in the body that is said to be associated with arterial sclerosis, they suppress supply of ubiquinone etc. associated with basal metabolism at the same time. It is reported that risks of cardiac infarct are immunologically decreased in some degree, while the onset ratio of cancer increases thereby increasing mortal ratio, which is an issue.

Concerning hypertension, antihypertensives lowering blood pressure with various inhibitors are sold additionally to the traditional calcium antagonists, and are forming a huge market. However, it is merely a symptomatic treatment which is not an approach to remove basic causes. Regarding antihypertensives, effectiveness of the administration is discussed concerning their immunological effectiveness or side effects.

Concerning impaired liver function, it is known that interferon treatment exhibits an effect for viral liver dysfunction. However, there is no effective means for a general decrease of liver function which is non-viral, and presently people are relying on nutritional supplements or folk medicine. It is empirically known that bear gall (Kumanoi) which was developed from Chinese herbal medicine has a certain effect, but the action mechanism as well as active ingredients is not specified. Many health foods are sold saying that freshwater clam or turmeric is effective, while the effect is not demonstrated. Further, an agent for improving liver function comprising sodium protoporphyrin as main ingredient has been used from a long time ago, but it is said that its effect is not sufficient, and photolesion is known as a side effect.

Concerning renal failure, dialysis is frequently performed during the treatment. However, it is to conduct renal function artificially, which is a prime example of a symptomatic treatment, not related with improvement of renal function. At present, for the improvement of renal function people are relying on nutritional supplements or folk medicine, as in the case of liver. Further, dialysis is the biggest cause of medical cost increase.

Adiposity is abominated as being the principal cause of all adult diseases. However, there is no suitable medicine, and dietary health foods suppressing absorption or digestion, or exercises are recommended, which are forming a giant market, causing not only financial but also mental burden. By taking the same amount of meal, a person gets certainly more weight with advancing age, compared to when young. This is not because absorption or digestion increases with advancing age, neither lack of exercise is the main cause, but it is because the basal metabolism is decreased. No approach to resolve adiposity by improving basal metabolism is known.

Concerning erectile dysfunction, an effective medicine called Viagra has been developed, which has improved life of many patients afflicted with erectile dysfunction. However, its action mechanism is dilation of blood vessels, and administration of Viagra leads physical erectile. However, the erection is not accompanied by an original emotion, and there is a risk of inducing cardiac diseases. Also in this field, folk medicines such as viper, rhinoceros horn, seal, or turtle are widely known. However, these folk medicines have no scientific nature, and rather many examples affecting health are known. Specifically, no basic approach focusing on the phenomenon that erection is weakened with advancing age is known.

Concerning menopausal disorder, generally, it is said to encompass malaise or depression induced by hormone imbalance in women after menopause. However, recently, it is known that menopausal disorder develops also in men, exhibiting symptoms including malaise and depression, similarly as women. When the case is severe, a treatment method comprising supplementing hormone is performed to men and women, which is effective. However, in case of women, a long time administration may increase risks of breast cancer or uterus cancer, or risks of cardiac infarct or cerebral stroke, which is an issue. In case of men, increase of risks of prostate cancer is an issue.

Concerning tension including shoulder discomfort and low back pain, although accurately it is not a disease but a symptom, there are many people suffering from shoulder discomfort and low back pain with advancing age. Treatment including acupuncture, jujutsu, massage, spa treatment etc; and medicines including poultice are forming a big business. There are many causes of tension such as shoulder discomfort and low back pain, of which stagnation of blood flow can be exemplified as one of main causes. Existing treatment and medicines are focusing on the improvement of blood flow. It is clear that no effective solution has been yet found out even though various means are proposed, from the fact that there are many people who are suffering from these symptoms with advancing age.

In the above, current status of adult diseases, and actual condition of therapeutic agents or treatment methods have been briefly explained. Generally, it can be said that decrease of basal metabolism with advancing age is the common cause or remote cause of adult diseases. It can be redefined to be remaining glucose or fat in blood caused by decrease of basal metabolism, leakage of active oxygen caused by impaired energy production system, and accumulation of gene defect caused thereby. Therefore, the basic treatment or prevention of adult diseases is related to how to keep the basal metabolism in a good state. However, as already stated, western medicine is an approach to treat with a biochemical inhibitor, which is merely a symptomatic treatment and not a radical treatment. Oriental medicine and traditional medicine have a basic idea that it is important to keep the fundamental basal metabolism, while specific solutions are within the range of breathing maneuver, body exercise, and use of traditional herbs, which effect is not sufficient.

In such conditions, development of a really effective therapeutic agent, treating method, preventive agent, and preventive method of adult diseases aiming to improve basal metabolism, with a scientific support and not being a merely symptomatic treatment is awaited.

On the other hand, ALA is known as an intermediate of pigment biosynthesis pathway, widely present in animals, plants, and bacteria, and is generally biosynthesized by 5-aminolevulinic acid synthase, from succinyl CoA and glycine. ALA itself does not have a photosensitization activity, but it is said to induce protoporphyrin IX (PpIX) via pigment biosynthesis pathway. Since it has been reported that by applying ALA and irradiating light, skin cancer can be treated (see for example, non-patent document 1), many methods for diagnosing and treating lesions of various sites using ALA have been reported. For example, an agent for diagnosing and treating tumors is prepared which has been developed from the fact that when ALA, its derivative, or salts thereof (hereinafter also referred to as "ALAs") is administered in the body, PpIX which is said to have tumor affinity is biosynthesized, and that when PpIX accumulated in tumor cells is irradiated with light, surrounding oxygen molecules are photoexcited, and that the resulting singlet oxygen has a cytotoxic effect due to its strong oxidative power (see for example patent documents 1 to 3).

Further, in bladder, it is known that it is possible to detect bladder cancer, by filling bladder with a radiosensitizing solution comprising ALAs via urethra, irradiating light after a certain time, and observing fluorescence with a microscope (see for example non patent document 2). Further, a hair restorer comprising an iron compound and one or more compounds selected from 5-aminolevulinic acid, its salt, or ester derivative thereof, as an active ingredient (see for example patent document 4), or an agent for preventing and ameliorating dry skin (see for example see patent document 5) has been proposed.

PRIOR ART DOCUMENTS

Patent Documents

Patent Document 1: Japanese Patent No. 2731032
Patent Document 2: Japanese Laid-Open Patent Application No. 2006-124372
Patent Document 3: Published Japanese translation of PCT International Publication No. 2002-512205
Patent Document 4: Japanese Patent No. 3810018
Patent Document 5: Japanese Patent No. 3991063

Non-Patent Documents

Non-Patent Document 1: J. C Kennedy, R. H Pottier and D C Pross, Photodynamic therapy with endogeneous protoporphyrin IX: basic principles and present clinical experience, J. Photochem., Photobiol. B: Biol., 6 (1990) 143-148
Non-Patent Document 2: Photodynamic diagnosis of bladder cancer, using fluorescent cytoscope, comprising injecting 5-aminolevulinic acid (5-ALA); Keiji Inoue, Nao Karashima, Masayuki Kamata, Taro Shuin, Atsushi Kurabayashi, Yuji Ohtsuki; Journal of Japanese Urological Association, Vol. 97, pp. 719-729

DISCLOSURE OF THE INVENTION

Object to be Solved by the Present Invention

The object of the present invention is to provide a pharmaceutical composition that can ameliorate or prevent an adult disease, by improving the basal metabolism which decreases with advancing age. Specifically, it is to provide a pharmaceutical composition which is different from an existing therapeutic agent for an adult disease inhibiting biochemical reactions, wherein the action mechanism is the improvement of basal metabolism, that is, the action mechanism is rejuvenation of metabolism, wherein the composition has no side effects, and does not generate drug resistance against adult disease; or to provide a method for preventing/treating adult diseases.

Means to Solve the Object

ALA is said to be one of the organic compounds that was generated on primitive earth 36 billion years ago, when energy of lightening has been imparted to the atmosphere. Tetrapyrrole compounds consisting of 8 ALA molecules, have a very long resonant system, and a high symmetry property of molecule. Thus, they can retain energy, and for example, they can absorb light energy.

Today, many reactions in which tetrapyrrole compounds are associated are known in the energy transducing system of organisms, and it is believed that ALA is a root substance of life. Many tetrapyrrole compounds are associated with life reaction, and for example, chlorophyll is a tetrapyrrole compound comprising magnesium in the center, which absorbs light energy. The reaction center of hemoglobin transporting oxygen is the tetrapyrrole compound heme coordinated with iron in the center. As the rate-limiting step of biosynthesis of chlorophyll or heme is ALA biosynthesis, a fertilizer comprising ALA and magnesium activates photosynthesis, and when ALA and iron are added to piglet's feed, anemia of the piglet is improved. The present inventors have already made these inventions and a part of them is already commercialized.

Research on human and ALA has a long history, and a study has been made when its neural toxicity has been suspected from the fact that a large amount of ALA was found in urine of patient suffering from hematoporphyria, a genetic disease. Further, it is used as an index of Industrial Safety and Health control, as a large amount of ALA is found in urine of patient suffering from heavy metal poisoning. As such, ALA had a rather bad image of being an index of disease, and being bad for health.

As an attempt for administering ALA to human, the diagnostic/therapeutic agent of cancer is well known, comprising administering ALA and accumulating protoporphyrin IX in cancer which is used in combination with light irradiation. It is called a photodynamic diagnosis, and photodynamic treatment, respectively, and is already practiced. Also in that case, ALA is rather known as a toxic substance that kills cancer cells, and no one estimated the effect of ameliorating or preventing adult diseases by improving the basal metabolism.

In the human body, ALA is biosynthesized by a condensation of glycine and succinyl CoA from an aminolevulinic acid synthetase in mitochondria. The biosynthesized ALA is once transported into cytoplasm, 2 molecules are condensed by an aminolevulinic acid dehydrogenase (porphobilinogen synthetase) in the cytoplasm, to form a pyrrole ring, and to form porphobilinogen. 4 molecules of porphobilinogen form a porphyrin ring to form a tetrapyrrole structure, and are converted sequentially with an enzyme in the cytoplasm, and become coproporphyrinogen III. Coproporphyrinogen III is uptaken into mitochondria by an ABC transporter, and oxygenated subsequently up to protoporphyrin IX. Divalent iron is coordinated by ferrochelatase, and becomes heme or cytochrome.

It is interesting that it is believed that the operation of mitochondria and somatic cell in cooperation, when forming heme or cytochrome, is associated with the birth of eukaryotes which is said to be 1.6 billion years ago with the symbiosis of mitochondria, and the evolution thereafter. Meanwhile, exogenously administered-ALA is converted to coproporphyrinogen in cytoplasma, similarly to endogenous ALA, and reaches into mitochondria. Heme or cytochrome that has been induced in mitochondria by ALA plays various important roles. Some are transported again to cytoplasm, conjugated with protein to play their role. The most important role of heme or cytochrome acting in mitochondria is the formation of an electron transport system. Heme or cytochrome is a constituting factor of complexes II, III and IV constituting the electron transport system. Cytochrome C transports electron directly from complex III to complex IV. Generally, it is said that length of human life is determined by the length of life of the electron transport system, particularly by the enzyme activity of complex IV. It is a good example showing the importance of the electron transport system which is an energy capture system. The reaction center of the electron transport system is cytochrome and heme induced by ALA.

The above shows that the decrease in the biosynthesizing ability of ALA in mitochondria with advancing age is the cause of aging, and is the basic cause of adult diseases. It was presumed that the basic mechanism is that the adult diseases ameliorate by administering ALA. The mechanism estimated for each symptom is discussed in the following.

When the intended adult disease is metabolic syndrome, it was thought that the primary action mechanism is that heme or cytochrome of the electron transport system is enhanced with the administration of ALA, preferably ALA and iron, and the so-called basal metabolism is improved.

When the intended adult disease is diabetes, it was thought that the primary action mechanism is that heme or cytochrome of the electron transport system is enhanced with the administration of ALA, preferably ALA and iron, and the so-called basal metabolism is improved. The TCA cycle functions suitably only when the electron transport system is activated. It was estimated that when TCA circuit functions, acetyl CoA which is the substrate is required, and sugar is consumed in the glycolytic system, leading to improvement of diabetes.

When the intended adult disease is hyperlipidemia, it was thought that the primary action mechanism is that heme or cytochrome of the electron transport system is enhanced with the administration of ALA, preferably ALA and iron, and the so-called basal metabolism is improved. The TCA cycle functions suitably only when the electron transport system is activated. It was estimated that when TCA cycle functions, acetyl CoA which is the substrate is required, and fatty acids are consumed by β-oxidation, leading to improvement of hyperlipidemia. Fatty acids are uptaken into mitochondria as acyl CoA, and are subjected to β-oxidation in the mitochondria. Further, when there is excessive sugar, fatty acids undergo a synthetic reaction in cytoplasm. However, as the sugar consumption is suppressed with the administration of ALA and iron, it can be expected that synthesis of fatty acids also lowers.

When the intended adult disease is hypertension, it is thought that the action mechanism is, in addition to the improvement of basal metabolism, that the generation of NO, a vasodilatory factor, is activated by heme enzyme, induced by ALA, preferably ALA and iron.

When the intended adult disease is impaired liver function, the action mechanisms are estimated to be, in addition to the improvement of basal metabolism, the ability of the liver to degrade toxic substances is enhanced with the administration of ALA, preferably ALA and iron. The degradation of toxic substances is a critical function of liver, which is induced by P450 having heme as a reaction center, wherein heme is induced by ALA, preferably ALA and iron.

When the intended adult disease is renal failure (impaired renal function), it is thought that the action mechanism is, in addition to the improvement of basal metabolism and improvement of blood flow by vascular dilatation, that the ion pump activity, which is a critical role of kidney, is activated with the increased level of heme or cytochrome, induced by ALA, preferably of ALA and iron.

When the intended adult disease is adiposity, it is thought that the primary action mechanism is that heme or cytochrome of the electron transport system is enhanced with the administration of ALA, preferably ALA and iron, and the basal metabolism is improved. It is believed that if it would be easier to start exercises again, which had become a pain, with age with the increase of basal metabolism, it would be useful for ameliorating adiposity.

When the intended adult disease is erectile dysfunction, the main action mechanism is the improvement of basal metabolism, and it is estimated that ALA has a critical action of enhancing male hormone secretion which decreases with age. The rate-limiting step of male hormone metabolism is the hydroxylation by cytochrome P450scc in the mitochondria. It is estimated that the activity of the enzyme is improved with the administration of ALA, preferably ALA and iron.

When the intended adult disease is menopausal disorder, the main action mechanism is the improvement of basal metabolism or vascular dilatation, and it is estimated that ALA has an action of enhancing sex hormone secretion which decreases with age. The rate-limiting step of sex hormone metabolism is the hydroxylation by cytochrome P450scc in the mitochondria, for male hormone as well as female hormone. It is estimated that the activity of the enzyme is improved with the administration of ALA, preferably ALA and iron.

When the intended adult disease is tension such as shoulder discomfort and low back pain, it is estimated that the improvement of congestion due to improvement of basal metabolism, and vascular dilatation involves a significant treatment effect.

As it is stated in the above, the present inventors addressed the basic issues which many biochemists have avoided, including, what is an adult disease, what is aging phenomenon, what is aging, or why decrease of basal metabolism with advancing age occurs. They arrived at a hypothesis, that the decrease of mitochondrial activity, more specifically the weakening of electron transfer system of mitochondria, induces a decrease of the energy capture efficiency, thereby a decrease of TCA cycle activity, which results in a decrease of sugar or lipid absorption, and induces adult diseases including diabetes, hyperlipidemia, adiposity, and metabolic syndrome. The present inventors further made a keen study, and made a hypothesis that the decrease of the activity of electron transfer system is caused by the decrease of heme compounds or cytochrome present in the pathway of electrons of the electron transfer system in mitochondria, which decrease is induced by the decrease of producing ability of ALA with advancing age. In order to confirm their hypothesis that the addition of ALA, which is a precursor of heme or cytochrome, which biosynthesis is a rate-limiting step of heme or cytochrome, and which production level decreases with advancing age, is effective as an agent for treating/preventing an adult disease, and that by using ALA, a method for treating adult diseases, or a method for preventing adult diseases could be established, the present inventors made continuous investigations on administration methods of ALA, kinds or amount of minerals to be combined. They confirmed that a composition comprising ALAs has an effect of treating/preventing adult diseases, and the present invention has been thus completed.

The present invention relates to: (1) a composition for preventing/ameliorating an adult disease comprising 5-aminolevulinic acid (ALA), its derivative, or salt thereof; and (2) the composition for preventing/ameliorating an adult disease according to (1), further comprising an iron compound; (3) the composition for preventing/ameliorating an adult disease according to (1) or (2), wherein the iron compound is one or more compounds selected from the group consisting of ferrous citrate, sodium ferrous citrate, iron sodium citrate, iron ammonium citrate, ferric pyrophosphate, heme iron, iron dextran, iron lactate, ferrous gluconate, DTPA iron, iron sodium diethylenetriaminepentaacetate, iron ammonium diethylenetriaminepentaacetate, iron sodium ethylenediaminetetraacetate, iron ammonium ethylenediaminepentaacetate, iron triethylenetetraamine, iron sodium dicarboxy-methylglutamic acid, iron ammonium dicarboxymethylglutamic acid ammonium, lactoferrin iron, transferrin iron, ferric chloride, iron sesquioxide, sodium iron chlorophyllin, ferritin iron, ferrous fumarate, ferrous pyrophosphate, saccharated iron oxide, iron acetate, iron oxalate, ferrous succinate, iron and sodium succinate citrate, iron sulfate, and sulfide glycine iron.

Further, the present invention relates to (4) the composition for preventing/ameliorating an adult disease according to any one of (1) to (3), wherein the adult disease is one or more diseases selected from the group consisting of metabolic syndrome, diabetes, hyperlipidemia, hypertension, impaired liver function, renal failure, adiposity, erectile dysfunction, menopausal disorder, shoulder discomfort, and low back pain; (5) a food or food product for preventing/ameliorating an adult disease, wherein the composition according to any one of (1) to (4) is added; (6) a method for using the composition according to any one of (1) to (4) for preparing an agent for preventing/ameliorating an adult disease; and (7) a method for preventing/ameliorating an adult disease, comprising administering the composition according to any one of (1) to (4).

BEST MODE FOR CARRYING OUT THE INVENTION

As for a composition for preventing/ameliorating (agent for preventing/ameliorating) an adult disease of the present invention, it is not particularly limited as long as it is a composition comprising ALAs constituted from ALA, its derivative, or salt thereof as an active ingredient or main ingredient. The above ALA is also referred to as δ-aminolevulinic acid, and is one of amino acids represented by the formula $HOOC-(CH_2)_2-(CO)-CH_2-NH_2$. These ALAs can be produced by any known methods such as chemical synthesis, production from microorganisms, or production from enzymes.

Among ALAs, as a derivative of ALA, for example a derivative comprising an ester group and acyl group of ALA can be exemplified. Preferably, a combination of methylester group and formyl group; methylester group and acetyl group; methylester group and n-propanoyl group; methylester group and n-butanoyl group; ethylester group and formyl group; ethylester group and acetyl group; ethylester group and n-propanoyl group; ethylester group and n-butanoyl group can be exemplified.

Among ALAs, examples of salts of ALA or its derivative include: acid addition salts such as hydrochloride, hydrobromide, hydroiodide, phosphate, nitrate, sulfate, acetate, propionate, toluenesulfonate, succinate, oxylate, lactate, tartate, glycolate, methanesulfonate, butyrate, valerate, citrate, fumarate, maleate, and malate; metal salts such as sodium salt, potassium salt, and calcium salt; ammonium salt, and alkyl ammonium salt. These salts are used as a solution when used, and it is preferred that the action is similar to that of ALA. These salts may form a hydrate or solvate, and it can be used separately, or by combining two or more of them.

In the present invention, an adult disease relates to a lifestyle disease which is strongly associated with lifestyle habits conducted for a long time. Suitable examples include metabolic syndrome, diabetes, hyperlipidemia, hypertension, impaired liver function, renal failure, adiposity, erectile dysfunction, menopausal disorder, shoulder discomfort, and low back pain.

A composition for preventing/ameliorating an adult disease of the present invention is preferred to further comprise an iron compound as an active ingredient. The iron compound in the present invention is not particularly limited as long as it is a compound having iron in its molecule. Examples include: ferrous citrate, sodium ferrous citrate, iron sodium citrate, iron ammonium citrate, ferric pyrophosphate, heme iron, iron dextran, iron lactate, ferrous gluconate, DTPA iron, iron sodium diethylenetriaminepentaacetate, iron ammonium diethylenetriaminepentaacetate, iron sodium ethylenediaminetetraacetate, iron ammonium ethylenediaminepentaacetate, iron triethylenetetraamine, iron sodium dicarboxymethylglutamic acid, iron ammonium dicarboxymethylglutamic acid ammonium, lactoferrin iron, transferrin iron, ferric chloride, iron sesquioxide, sodium iron chlorophyllin, ferritin iron, ferrous fumarate, ferrous pyrophosphate, saccharated iron oxide, iron acetate, iron oxalate, ferrous succinate, iron and sodium succinate citrate, iron sulfate, and sulfide glycine iron. Among these, ferrous citrate and iron sodium citrate are preferred. These iron compounds can be used separately, or by combining 2 or more of them. The iron compound contained in a composition for preventing/ameliorating an adult disease of the present invention is usually 0 to 100-fold the administration level of ALA in molar ratio, and preferably 0.1 to 8-fold.

A composition for preventing/ameliorating an adult disease of the present invention is useful as an agent for preventing/ameliorating an adult disease, and can be used as an oral administration type, or intravenous injection type. As for a formulation of an agent for preventing/ameliorating an adult disease of an oral administration type, examples include powder, granule, tablet, capsule, syrup, and suspension. As for a formulation of intravenous injection type, injection and intravenous fluid can be exemplified. When preparing a composition for preventing/ameliorating an adult disease of the present invention as an aqueous solution for injection, etc., it is preferred to prepare with attention so that the aqueous solution does not become alkaline in order to prevent degradation of ALAs. In case it becomes alkaline, degradation of active ingredients can be prevented by removing oxygen.

A composition for preventing/ameliorating an adult disease of the present invention can be further supplemented with other optional components such as medicinal components, nutritional supplements, and carriers as necessary. Optional components include, pharmaceutically acceptable normal carrier, binding agent, stabilizer, solvent, dispersant, bulking agent, excipient, diluent, pH buffer, disintegrant, solubilizer, solubilizing agent, and isotonic agent, such as crystalline cellulose, gelatine, lactose, starch, magnesium stearate, talc, vegetable and animal fat, fat and oil, gum, and polyalkylene glycol.

Among ALAs contained in an agent for preventing/ameliorating an adult disease of the present invention, the most preferred are ALA, ALA methylester, ALA ethylester, ALA propylester, ALA butylester, ALA pentylester, and hydrochloride, phosphate and sulfate of these ALA esters.

A preferred method for administering an agent for preventing/ameliorating an adult disease of the present invention, include oral administration comprising sublingual administration; intravenous injection comprising intravenous fluid; and transdermal administration by poultice, or suppository. The amount of ALAs contained in these agents for preventing/ameliorating an adult disease may be 0.1 mg to 1000 mg in terms of ALA hydrochloride per day for adult, preferably 0.3 mg to 300 mg, more preferably 1 mg to 100 mg. The time for administrating the agent for preventing/ameliorating an adult disease of the present invention is not particularly limited, and it may be administered in the morning or in the afternoon. When the administration quantity is large, it is preferred to be administered in several times.

The agent for preventing/ameliorating an adult disease of the present invention may be used by combining with other agents for preventing, ameliorating, or treating an adult disease. As existing medicines of this field are inhibitors of a particular reaction, and have a different action mechanism from that of the agent of the present invention which enhances basal metabolism, an additive effect, and in some cases synergistic effect can be expected by using them in combination.

As for a food or food material for preventing/ameliorating an adult disease of the present invention, it is not particularly limited as long as the above composition for preventing/ameliorating an adult disease of the present invention is added. By adding a composition of the present invention containing ALAs to food or drink, a food or food material for preventing/ameliorating an adult disease can be made. Further, as for a method for using the present invention, it is not particularly limited as long as it is a method for using a composition for preventing/ameliorating an adult disease for preparing an agent for preventing/ameliorating an adult disease. A method for using a composition of the present invention comprising ALAs for preparing an agent for preventing/ameliorating an adult disease, can be exemplified by a method for preparing an agent for preventing/ameliorating an adult disease of an oral administration type or intravenous injection type by compounding the above optional components to ALAs. Further, as a method for preventing/ameliorating an adult disease of the present invention is not particularly limited as long as it is a method comprising administrating a composition for preventing/ameliorating an adult disease of the present invention. The administration method can be exemplified by oral administration, intravenous injection, and transdermal administration, as is stated in the above.

Embodiment of a food or food material for preventing/ameliorating an adult disease of the present invention include: a food or food material added with ALAs, with a label stating that it can be used for preventing/ameliorating an adult disease; a method for using a food or food material added with ALAs, as a food or food material for preventing/ameliorating an adult disease; a method for using ALAs as a compounding agent of a food or food material for preventing/ameliorating an adult disease; a method for manufacturing food or food material for preventing/ameliorating an adult disease, comprising adding ALAs to the food or food material.

As a food or food material for preventing or ameliorating an adult disease of the present invention include: various drinks such as yoghurt, drink yoghurt, juice, milk, soy milk, alcohols, coffee, red tea, boiled tea (sencha), oolong tea, and sport drink; baked confectionery such as pudding, cookie, bread, cake, jelly, and rice cake; Japanese cakes such as faded black; breads and snacks such as cold desserts and chewing gum; noodles such as wheat noodle and buckwheat noodle; fish cakes such as steamed fish paste, ham, fish meat sausage; seasonings such as soybean paste (miso), soybean sauce, dressing, mayonnaise, sweetener; dairy products such as cheese and butter; soy bean cake (tofu), yam paste, various prepared foods such as fish boiled in soy sauce, kop-zi, cro­quette, and salad; and nutritional foods. "For preventing/ameliorating an adult disease" means that the use of ALAs is intended for preventing/ameliorating an adult disease, such as being indicated on the package or instructions of the food or food material that it is effective for preventing/ameliorating an adult disease.

In the following, the present invention will be further explained, while the present invention is not limited to these Examples.

Example 1

A 61 years-old male ingested 1 capsule comprising 5 mg of aminolevulinic acid phosphate (5-aminolevulinic acid phos­phate) and 2.87 mg of sodium ferrous citrate each morning and afternoon, and improvement of the following biochemi­cal values was observed in 2 weeks.

| | |
|---|---|
| TG | 314 → 132 |
| GOT | 19 → 19 |
| GPT | 17 → 15 |
| γ-GTP | 60 → 48 |
| HbA1c | 6.2 → 5.9 |

Lipid metabolism, liver function, and sugar metabolism were all improved. Particularly, lipid metabolism was improved to a normal level, and a treatment effect was clearly shown. It was shown from this Example that the administra­tion of ALA is effective for various adult diseases.

Example 2

A 60 years-old male ingested 1 capsule comprising 5 mg of aminolevulinic acid phosphate and 2.87 mg of sodium ferrous citrate per day, and improvement of the following biochemi­cal values was observed 1 month after.

| | |
|---|---|
| TC | 264 → 260 |
| LDL | 192 → 173 |
| HDL | 65 → 58 |

It was shown from this example that the administration of ALA is effective for improving lipid metabolism and liver function.

Example 3

A 73 years-old male ingested 1 capsule comprising 5 mg of aminolevulinic acid phosphate and 2.87 mg of sodium ferrous citrate per day, and hypertension was ameliorated. 1 month after, he stopped taking antihypertensives which he had been taking until then, but the blood pressure maintained a normal level. It was shown from this example that the administration of ALA is effective for hypertension.

Example 4

A 70 years-old male being a borderline diabetes patient ingested 1 capsule comprising 5 mg of aminolevulinic acid phosphate and 2.87 mg of sodium ferrous citrate per day, and improvement of the following biochemical values was observed 1 month, 2 months, and 3 months after initiating ingestion.

| | Before initiation | After 1 month | After 2 months | After 3 months |
|---|---|---|---|---|
| HbA1c | 7.4 | 7.2 | 6.9 | 6.8 |

It was shown by this example that administration of ami­nolevulinic acid is effective for amelioration and prevention of diabetes.

Example 5

A 68 years-old male ingested 1 capsule comprising 5 mg of aminolevulinic acid phosphate and 2.87 mg of sodium ferrous citrate per day. Improvement of shoulder discomfort from which he was suffering for a longtime was observed from 1 week after initiating ingestion. It was shown from this example that administration of aminolevulinic acid is effec­tive for tension such as shoulder discomfort.

Example 6

A 42 years-old male ingested 1 capsule comprising 5 mg of aminolevulinic acid phosphate and 23 mg of sodium ferrous citrate per day. From the day after initiating ingestion, ame­lioration of migraine which he suffered since he was 40 years of age was observed. After 1 week of ingestion, migraine was completely cured. This shows that administration of aminole­vulinic acid is effective for male menopause.

Example 7

A 47 years-old male ingested 2 capsules each comprising 5 mg of aminolevulinic acid phosphate and 2.87 mg of sodium ferrous citrate per day. The next morning, erection which was not observed for a long time was observed. The next day of ingestion, he had sexual intercourse for the first time in a year, and since then, he continuously has sexual intercourse once every 2 weeks on average. This shows that administration of aminolevulinic acid is effective for erectile dysfunction, and also effective for preventing mental depression accompanied with aging.

Example 8

A 45 years-old male ingested 2 capsules each comprising 5 mg of aminolevulinic acid phosphate and 23 mg of sodium ferrous citrate per day. From the day following the ingestion, he felt fulfilled physically and mentally. Three days after initiating ingestion, he had sexual intercourse for the first time in half a year, and after that, he continuously has sexual intercourse twice a week on average. This shows that admin­istration of aminolevulinic acid is effective for erectile dys­function, and also effective for preventing mental depression accompanied with aging.

Example 9

A 47 years-old male ingested 1 capsule comprising 50 mg of aminolevulinic acid phosphate and 57.4 mg of sodium ferrous citrate per day. From the day following the ingestion, he felt fulfilled physically and mentally. By measuring his temperature with a female thermometer, an increase of 0.1 to 0.2° C. was observed compared to before ingestion. After 3 months of ingestion, his body weight decreased by 5 kg from 79 kg to 74 kg, and gray hair and crimples were also ameliorated. This shows that administration of aminolevulinic acid is effective for adult diseases such as metabolic syndrome.

Example 10

A 46 years-old female suffering from sensitivity to cold temperature, ingested 1 capsule comprising 5 mg of aminolevulinic acid phosphate and 2.87 mg of sodium ferrous citrate per day. From 2 days after initiating ingestion, she felt warmth to her limbs, and the sensitivity to cold temperature was ameliorated, and constipation was not observed. This shows that administration of aminolevulinic acid is effective for sensitivity to cold temperature and constipation.

Example 11

A 55 years-old female suffering from menopausal disorder, ingested 2 capsules each comprising 5 mg of aminolevulinic acid phosphate and 23 mg of sodium ferrous citrate per day. From 1 week after initiating ingestion, she felt improvement of physical strength and facial rejuvenation, and that symptoms of menopausal disorder such as hot-flash or frustration were gone. This shows that administration of aminolevulinic acid is effective for menopausal disorder.

Example 12

A 47 year-old male suffering from shoulder discomfort, applied 1 wt % each of aminolevulinic acid phosphate and DTPA iron (diethylene triamine penta acetic acid)-Fe) once a day to the sites of low back pain and shoulder discomfort, and shoulder discomfort was gone in a week.

Example 13

After obtaining informed consent before the initiation of the test, 30 men and women of age 22 to 63 participated in a double-blind test, and ingested a soft capsule comprising ALA phosphate, and ALA phosphate and ferrous citrate. Groups I, II, and III all ingested 1 capsule per day continuously for 4 weeks. The capsule of Group I comprised 5 mg of ALA phosphate; the capsule of Group II comprised 15 mg of ALA phosphate; and the capsule of Group III comprised 5 mg of ALA phosphate and 2.87 mg of ferrous citrate. Biochemical examination of blood was performed 2 weeks and 4 weeks after initiating ingestion, and 2 weeks after the end of the test. The following items showed a significant change in the biochemical examination of blood.

1) ALP
Group II showed a decrease of 18.0±23.2 U/L in 2 weeks (195.2±74.7 vs 177.2±55.2 U/L).
2) Total Proteins
Group II showed a decrease of 0.29±0.22 g/dL in 4 weeks (7.28±0.48 vs 6.99±0.47 g/dL).
3) Albumin
Group III showed a decrease of 0.12±0.11 g/dL in 2 weeks (4.43±0.26 vs 4.31±0.26 g/dL).
4) Creatinine
Group II showed a decrease of 0.040±0.037 mg/dL in 4 weeks (0.701±0.134 vs 0.661±0.109 mg/dL)
5) Total Cholesterol
Group III showed a decrease of 13.2±15.0 mg/dL in 2 weeks (204.1±21.0 vs 190.9±30.3 mg/dL).

6) HDL-Cholesterol
Group I showed a decrease of 3.7±4.9 mg/dL in 4 weeks (64.6±17.3 vs 60.9±15.8 mg/dL).
Group III showed a decrease of 2.6±2.8 mg/dL in 2 weeks (67.8±12.4 vs 65.2±11.7 mg/dL).
2 weeks after the end of the test, the level decreased by 2.8±3.7 mg/dL (67.8±12.4 vs 65.0±11.4 mg/dL).
7) LDL-Cholesterol
Group III showed a decrease of 10.7±7.8 mg/dL in 2 weeks (122.5±20.6 vs 111.8±25.9 mg/dL).
8) Na
Group III showed an increase of 0.7±0.7 mEq/L, 2 weeks after the end of the test (140.4±1.6 vs 141.1±1.5 mEq/L).

Decrease of ALP is a favorable change showing amelioration of liver function, and decrease of total protein, alubumin, and creatinine shows the improvement of protein metabolism. Further, decrease of total cholesterol, HDL-cholesterol, LDL-cholesterol is a favorable change showing that lipid metabolism is heading to amelioration. It can be estimated that increase of sodium is related to sodium discharge from cells, and improvement of kidney function can be expected.

The above tests were conducted to healthy subjects, but metabolisms related to adult diseases showed a good tendency. Thus, the effect of prevention/amelioration of the present invention was shown.

Example 14

Figure 1:
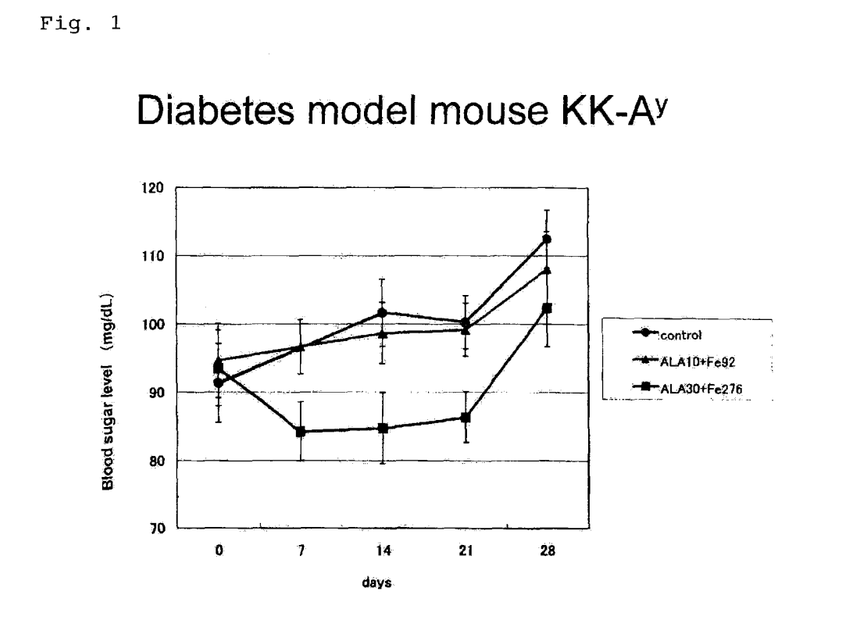
FIG. 1 It is a graph showing the change of blood sugar level by ALA administration using diabetes mouse models.
Figure 2:
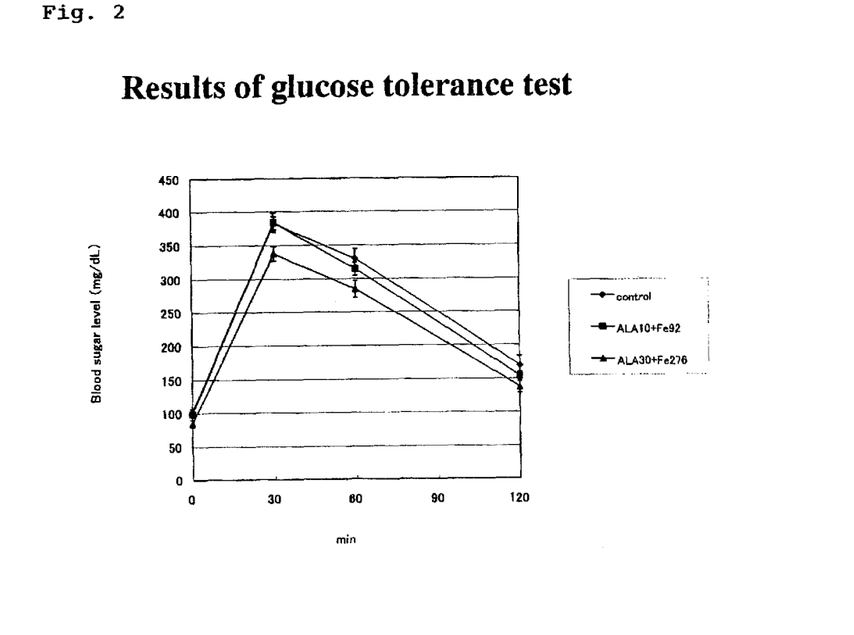
FIG. 2 It is a graph showing the results of glucose tolerance test by ALA administration using diabetes mouse models.
Figure 3:
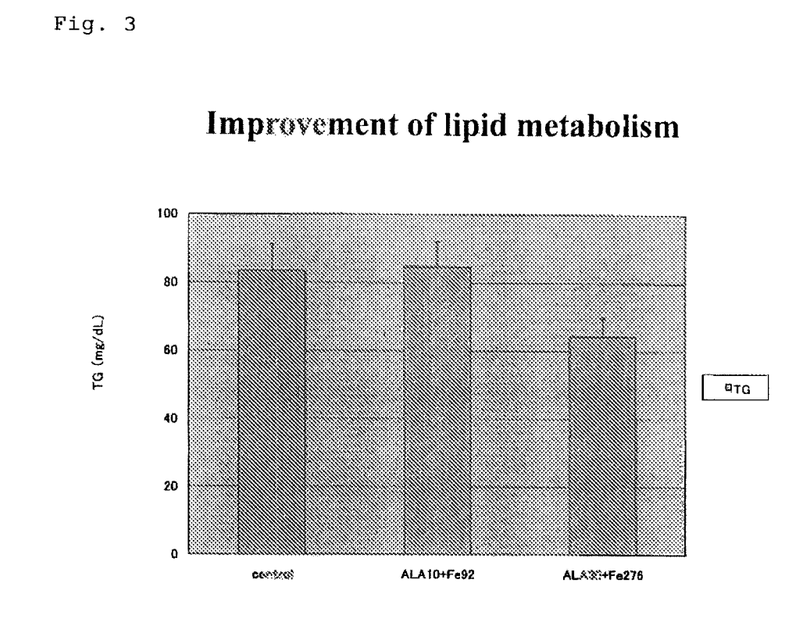
FIG. 3 It is a graph showing the lipid change by ALA administration using diabetes mouse models.
Figure 4:
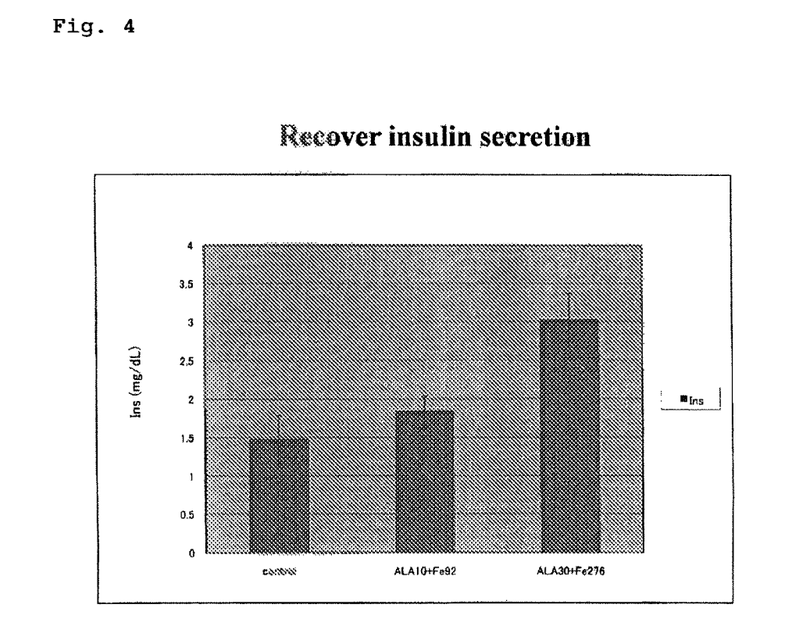
FIG. 4 It is a graph showing the change of insulin secretion level by ALA administration using diabetes mouse models.

Naturally occurring-type II diabetes mouse models, KK-Ay mice, were bred according to a common method, and made to have obesity. FIG. 1 shows the blood sugar levels of when 10 mg of 5-aminolevulinic acid (ALA) and 92 mg of sodium ferrous citrate (iron citrate) per 1 kg of body weight; and when 30 mg of ALA and 276 mg of iron citrate per 1 kg of body weight were administered to the mice. FIG. 2 shows the results of glucose tolerance test; FIG. 3 shows the transition of neutral fat during this period; and FIG. 4 shows the development of insulin secretion during this period. Each experiment was conducted with 10 mice.

As it is clear from the figures, by administering ALA and iron, blood sugar levels decreased, sugar tolerance ability increased, lipid metabolism increased and insulin secretion was ameliorated, suggesting that the administration was effective for diabetes and dyslipidemia. General drug for improving diabetes worsen lipid metabolism, while ALA and iron activated mitochondrial electron transfer system, and improved chained rotation of TCA cycle. Therefore, the so-called basal metabolism was improved, and it is assumed that consumption of both sugar and lipid has improved.

Example 15

Figure 5:
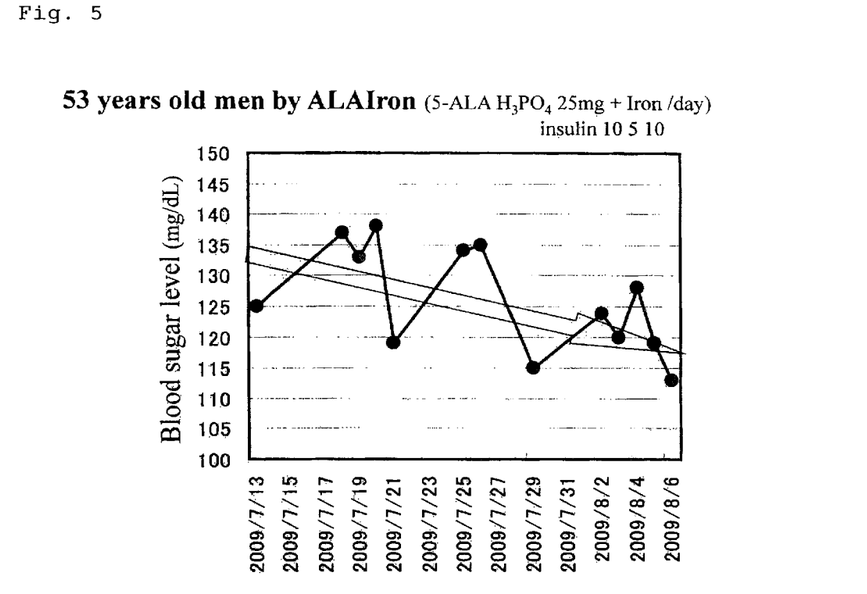
FIG. 5 It is a graph showing the change of fasting blood sugar by ALA administration in a diabetes patient.

A 53 year-old type II diabetes patient was having insulin treatment, and was administered insulin in an amount of 10 units in the morning, 5 units at noon, and 10 units in the evening. FIG. 5 shows the change of fasting blood sugar when 25 mg of ALA phosphate and iron citrate in an amount of 0.5-fold in molar ratio of ALA per day were administered to this patient.

The fasting blood sugar differs significantly depending on the diet of the previous day, increasing and decreasing, while as it is shown by the auxiliary line, it decreased averagely by about 15 mg/dl in 1 month, showing to be effective for ameliorating diabetes.

Example 16

Figure 6:
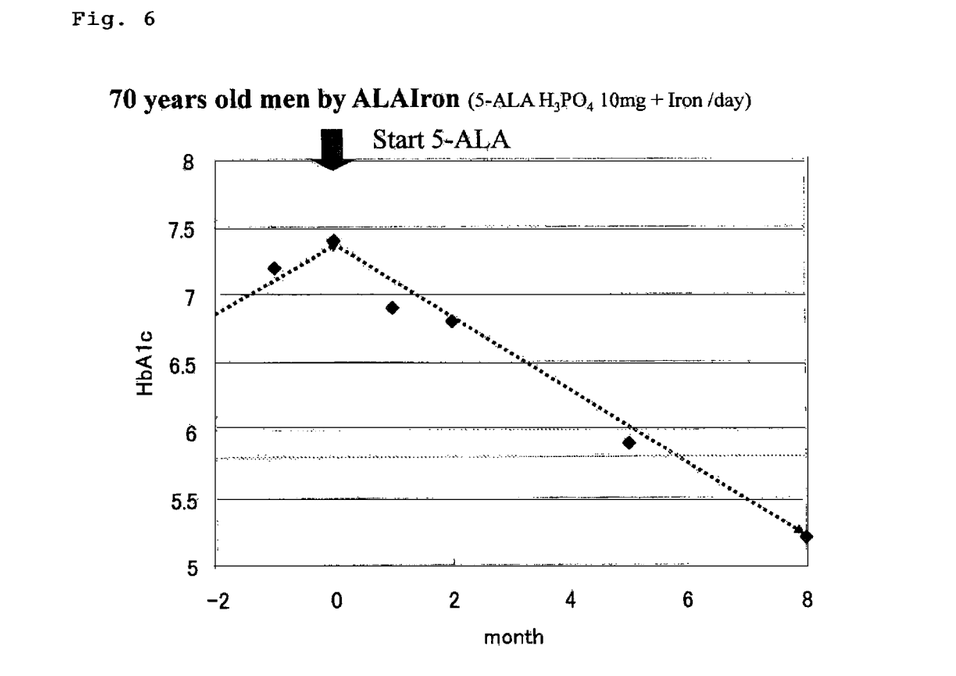
FIG. 6 It is a graph showing the change of glycated hemoglobin by ALA administration in a borderline diabetes patient.

The male patient of Example 4 continued ingestion under the same conditions. Five months after the initiation of administration, HbA1c decreased to 5.9, and further decreased to 5.2 eight months later, and he was completely free of diabetes. The results are shown in FIG. 6.

Example 17

Figure 7:
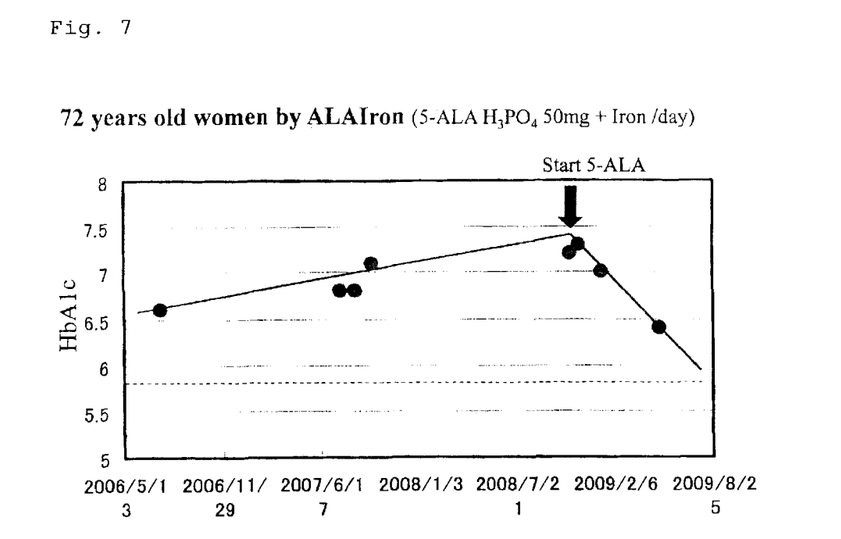
FIG. 7 It is a graph showing the change of glycated hemoglobin by ALA administration in a borderline diabetes patient.

A 72 years-old woman suffering from type II diabetes, had been living being careful of her eating habit and taking exercises under the guidance of her doctor, while HbA1c increased gradually. On Nov. 7, 2008, she started to ingest 50 mg of ALA phosphate and iron citrate in an amount of 0.5-fold in molar ratio of ALA per day. A rapid improvement of HbA1c was observed, and her condition improved in 6 months. The development during this time period is shown in FIG. 7. Meanwhile, the fasting blood sugar level on Nov. 7, 2008, at the time of initiation of ingestion was 195 mg/dl, which was ameliorated to 107 mg/dl on May 9, 2009.

Example 18

Figure 8:
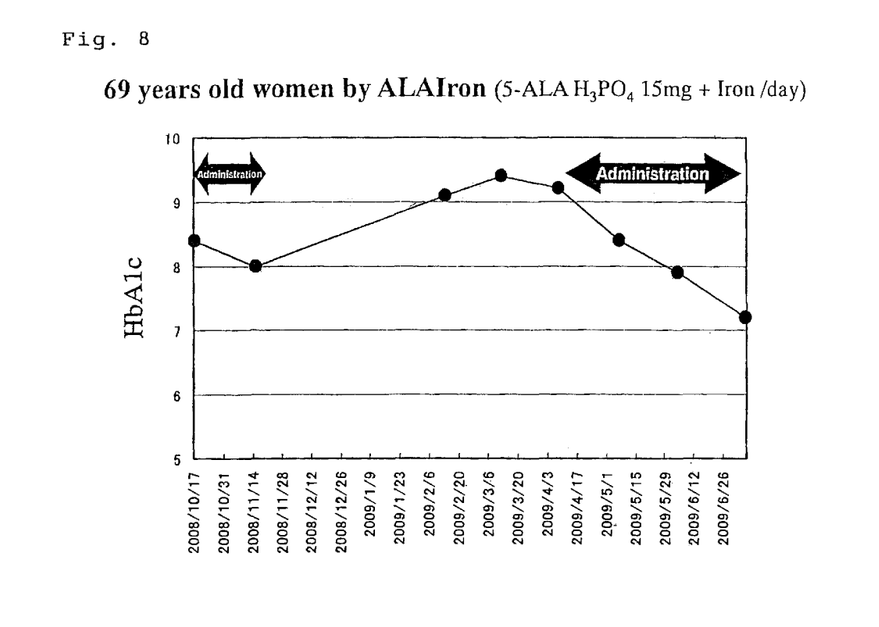
FIG. 8 It is a graph showing the change of glycated hemoglobin with and without ALA administration in a diabetes patient.

A 69 years-old woman having type II diabetes started to digest 15 mg of ALA phosphate and iron citrate in an amount of 0.5-fold in molar ratio of ALA per day, interrupted the ingestion once, and then restarted the ingestion. FIG. 8 shows the change of HbA1c during this time period. Bold arrow shows the ingested period. HbA1c is ameliorated by ingestion. As HbA1c increased when the ingestion was interrupted, it has been clarified that it is an effect exhibited by ALA.

Example 19

Figure 9:
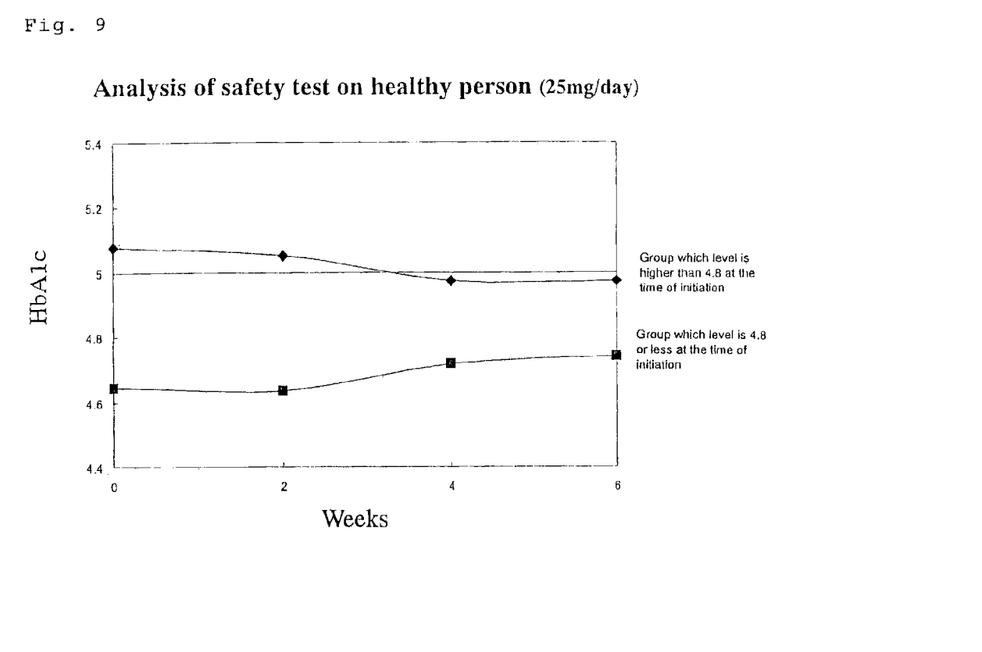
FIG. 9 It is a graph showing the change of glycated hemoglobin by ALA administration per group in a safety test on healthy person.
Figure 10:
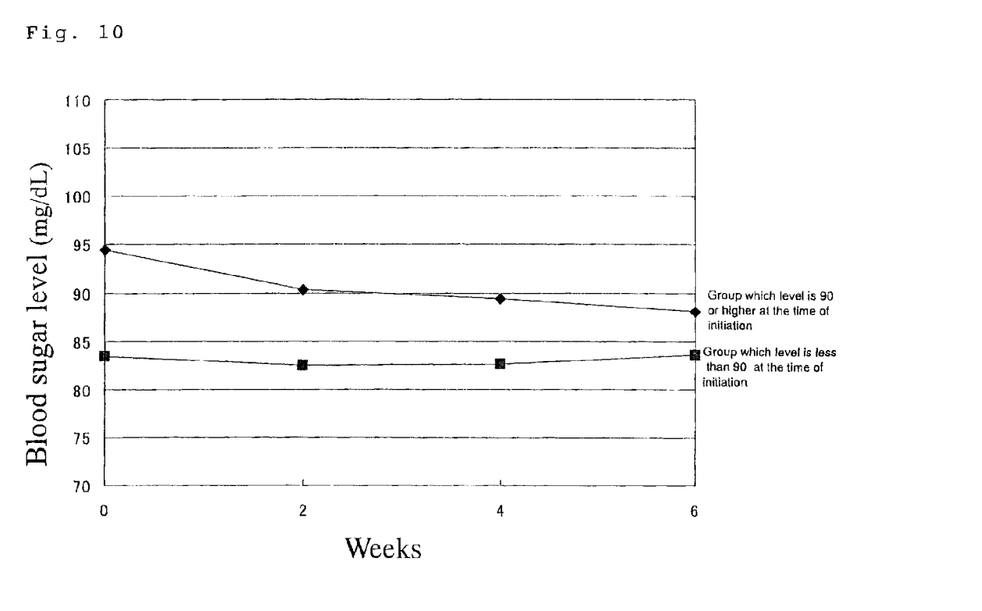
FIG. 10 It is a graph showing the change of blood sugar level by ALA administration per group in a safety test on healthy person.

As a safety test, healthy subjects started to ingest 25 mg of ALA phosphate and iron citrate in an amount of 0.5-fold in molar ratio of ALA per day, which ingestion was continued for 4 weeks. Blood was tested every two weeks including before ingestion, and after termination of ingestion. No significant change was observed in average levels. Further, the stratified results of healthy subjects which were divided into a group in which HbA1c before ingestion was higher than 4.8, and a group in which HbA1c before ingestion was 4.8 or less are observed in FIG. 9. As it is shown from FIG. 9, some decreasing tendency was shown in the group with HbA1c higher than 4.8, while a rather increasing tendency was observed for the group of 4.8 or less, suggesting that it is an effect with high safety, which does not affect healthy subjects. Similarly, change of blood sugar level when the subjects were divided into a group with fasting blood sugar level of 90 or more, and a group with a level of less than 90 is shown in FIG. 10. As it is clear from FIG. 10, a mild decrease is observed for the group having a relatively high level within the normal range, while almost no change is observed in the lower group, suggesting that it is an effect with high safety, which does not affect healthy subjects.

Example 20

The ingested amount of ALA, ingested period, and HbA1c change of 6 male borderline diabetes patients are shown in Table 1. HbA1c was ameliorated in all of 6 patients, showing that the present invention is highly probable.

TABLE 1

Results of pilot study in diabetes patients by 5-ALA

| age | sex | amount mg/day | period month | before | after |
|-----|-----|---------------|--------------|--------|-------|
|     |     |               |              | HbA1c(%) | |
| 47 | men | 50 | 3 | 6.1 | 5.7 |
| 45 | men | 50 | 2 | 7.5 | 6.1 |
| 40 | men | 50 | 2 | 7.5 | 6.1 |
| 58 | men | 10 | 2 | 6.7 | 5.7 |
| 70 | men | 10 | 8 | 7.4 | 5.2 |
| 61 | men | 10 | 0.5 | 6.2 | 5.9 |

INDUSTRIAL APPLICABILITY

According to the present invention, it is possible to improve or prevent an adult disease by improving basal metabolism which decreases with advancing age. The present invention is different from an existing therapeutic agent of an adult disease, of a biochemical reaction-inhibiting type, and its action mechanism is to increase the basal metabolism, in other words its action mechanism is the rejuvenation of metabolism, and has no side effect, and does not generate drug resistance. Further, as the action mechanism is different from that of an existing drug, it is expected that its effect can be enhanced by using in combination with an existing drug.

The invention claimed is:

1. A method for treating an adult disease, comprising administering a composition consisting essentially of 5-aminolevulinic acid (ALA), its ester derivative or acyl derivative, or a salt thereof to a subject in need thereof, wherein adult disease is diabetes.

2. A method for treating an adult disease, comprising administering a composition consisting essentially of (i) 5-aminolevulinic acid (ALA), its ester derivative or acyl derivative, or a salt thereof, and (ii) an iron compound to a subject in need thereof, wherein the adult disease is disease.

3. The method according to claim 2, wherein the iron compound is one or more compounds selected from the group consisting of ferrous citrate, sodium ferrous citrate, iron sodium citrate, iron ammonium citrate, ferric pyrophosphate, heme iron, iron dextran, iron lactate, ferrous gluconate, DTPA iron, iron sodium diethylenetriaminepentaacetate, iron ammonium diethylenetriaminepentaacetate, iron sodium ethylenediaminetetraacetate, iron ammonium ethylenediaminepentaacetate, iron triethylenetetraamine, iron sodium dicarboxymethylglutamic acid, iron ammonium dicarboxy methylglutamic acid ammonium, lactoferrin iron, transferrin iron, ferric chloride, iron sesquioxide, sodium iron chlorophyllin, ferritin iron, ferrous fumarate, ferrous pyrophosphate, saccharated iron oxide, iron acetate, iron oxalate, ferrous succinate, iron and sodium succinate citrate, iron sulfate, and sulfide glycine iron.

* * * * *

UNITED STATES PATENT AND TRADEMARK OFFICE
CERTIFICATE OF CORRECTION

| | | |
|---|---|---|
| PATENT NO. | : 9,095,165 B2 | Page 1 of 1 |
| APPLICATION NO. | : 13/123374 | |
| DATED | : August 4, 2015 | |
| INVENTOR(S) | : Tohru Tanaka | |

It is certified that error appears in the above-identified patent and that said Letters Patent is hereby corrected as shown below:

In the claims

Col. 16, claim 1, line 34, "wherein adult" should be --wherein the adult--.

Col. 16, claim 2, line 40, "disease is disease" should be --disease is diabetes--.

Signed and Sealed this
Fifth Day of January, 2016

Michelle K. Lee
*Director of the United States Patent and Trademark Office*